United States Patent
Kwon (10) Patent No.: US 6,983,660 B2
(45) Date of Patent: Jan. 10, 2006

(54) FATIGUE MEASUREMENT DEVICE AND METHOD

(76) Inventor: Young Wuk Kwon, 3008 W. Sunset Dr. - Apt. A, Carbondale, IL (US) 62901

(*) Notice: Subject to any disclaimer, the term of this patent is extended or adjusted under 35 U.S.C. 154(b) by 0 days.

(21) Appl. No.: 10/700,236

(22) Filed: Nov. 3, 2003

(65) Prior Publication Data

US 2004/0216530 A1 Nov. 4, 2004

Related U.S. Application Data

(60) Provisional application No. 60/466,379, filed on Apr. 29, 2003.

(51) Int. Cl.
*G01N 3/00* (2006.01)

(52) U.S. Cl. .............................. 73/806; 73/807; 73/808

(58) Field of Classification Search ................. 73/760, 73/762–791, 806–808, 861.22, 861.24, 861.83, 73/861.356, 861.357, 861.355
See application file for complete search history.

(56) References Cited

U.S. PATENT DOCUMENTS

| | | |
|---|---|---|
| 2,920,480 A | 1/1960 | Haas |
| 3,088,083 A | 4/1963 | Ward |
| 3,136,154 A | 6/1964 | Christensen |
| 3,272,003 A | 9/1966 | Harting |
| 3,572,091 A | 3/1971 | McFarland |
| 3,780,817 A | 12/1973 | Videon |
| 3,782,178 A | 1/1974 | Thomas |
| 3,786,679 A | 1/1974 | Crites |
| 3,979,949 A | 9/1976 | Smith |
| 4,081,993 A | 4/1978 | Leonhardt et al. |
| 4,107,980 A | 8/1978 | Crane et al. |
| 4,186,599 A | 2/1980 | Frick ............................. 73/194 |
| 4,409,841 A | 10/1983 | Archer |
| 4,580,520 A | 4/1986 | Archer |
| 4,590,804 A * | 5/1986 | Brull ............................ 73/762 |
| 4,639,997 A | 2/1987 | Brull |
| 4,841,781 A * | 6/1989 | Khalifa ...................... 73/861.22 |
| 4,926,695 A | 5/1990 | Kleven et al. ............ 73/861.24 |
| 5,237,875 A | 8/1993 | de la Veaux |
| 5,319,982 A | 6/1994 | Creager |
| 5,425,274 A | 6/1995 | Creager |
| 5,520,055 A | 5/1996 | Füssinger |
| 5,528,151 A | 6/1996 | Perez |
| 5,614,680 A | 3/1997 | Füssinger |
| 5,816,530 A | 10/1998 | Grube |
| 6,053,053 A | 4/2000 | Huotari .................... 73/861.22 |
| 6,199,434 B1 * | 3/2001 | Cornil et al. ............. 73/861.83 |
| 6,257,071 B1 * | 7/2001 | Dessert et al. ........... 73/861.22 |
| 6,408,700 B1 * | 6/2002 | Matt et al. .............. 73/861.356 |
| 6,443,018 B1 | 9/2002 | Lee et al. |
| 6,578,430 B1 * | 6/2003 | Duerr ........................... 73/787 |

OTHER PUBLICATIONS

Product Data Sheet, Dec. 2001, Model 8800C, Model 8800C Smart Vortex Flowmeter, of Emerson Process Management, pp. 1-27.

* cited by examiner

*Primary Examiner*—Max Noori
*Assistant Examiner*—Alandra Ellington (57) ABSTRACT

An apparatus and method for measuring the fatigue strength and fatigue damage of structures and predicting the service life remaining in the structure being tested. The apparatus is a specially designed fatigue gauge that contains breakable ligaments of either variable length to measure fatigue strength or fatigue damage of metallic, polymeric and composite materials or the same length but different composition to measure the fatigue strength and fatigue damage of certain composite materials.

13 Claims, 6 Drawing Sheets

FIG. 3(a) Plane View

FIG. 3(b) Sectional View

FATIGUE MEASUREMENT DEVICE AND METHOD

CROSS-REFERENCE TO RELATED APPLICATION

This application claims the benefit of Provisional Patent Application Ser. No. 60/466,379 filed Apr. 29, 2003.

FEDERALLY SPONSORED RESEARCH

Not Applicable

SEQUENCE LISTING OR PROGRAM

Not Applicable

BACKGROUND

1. Field of Invention

This invention relates to a device for measuring fatigue strength and fatigue damage of metallic and composite structures and to a method for predicting the service life remaining on those metallic and composite structures to which the measuring device is attached.

2. Description of the Prior Art

Structural and design engineers must be able to determine the fatigue strength and fatigue life of any material that is used or being considered for use as a load-carrying component and which is or will be subjected to a repetitive or cyclic stress loading condition. This requirement stems from the fact that repetitive stress on a structure will eventually cause a material failure in that structure due to fatigue in the material comprising the structure being tested. Further, as a load-carrying structure is subjected to repetitive cyclic loads, structural and design engineers must be able to monitor the effects of these load conditions to determine the remaining service life of the structural member so as to take it out of service before failure occurs.

Engineers have extensively studied the fatigue life of structural materials to more accurately determine the current state of fatigue damage and to more accurately predict the remaining service life in these structures. These studies have shown that fatigue strength is a function of the material comprising the mechanical or metal structure being tested or measured, the manner in which that material has been treated, the ambient temperature in which the structure exists or operates, the amount of stress applied to the structure, and the number of stress cycles the test member undergoes. These studies have also shown that such structures are subject to fatigue failure when they are subjected to repetitive stresses that are lower in magnitude than the ultimate stress of the materials making up the structures being tested. Further, these studies have shown that the service life of a given structural material is inversely proportional to the applied stress; i.e., the greater the applied stress, the shorter the service life of the structural material.

To determine the current state of fatigue damage and/or predict the remaining service life in these structures, test engineers have typically relied upon any number of fatigue monitoring devices such as the fatigue detectors, fuses, gauges, indicators, monitors, predictors, sensors, testers, and transducers taught by the prior art. These conventional devices are typically attached to the structure being monitored so that the test elements are aligned with the direction of the maximum principal stress applied to the structure being tested. As such, these conventional fatigue measuring and/or monitoring devices were capable of monitoring fatigue damage in only one fixed direction. Further, these earlier fatigue gauges typically contained only one test element which necessitated multiple tests on the structure being tested or, alternatively, the attachment of multiple gauges to obtain the desired values of fatigue damage or service life remaining.

Those that contained multiple test elements such as U.S. Pat. No. 3,572,091 issued to McFarland (1971), U.S. Pat. No. 5,319,982 issued to Creager (1994) and U.S. Pat. No. 5,425,272 also issued to Creager (1995) were limited by the costly or time-consuming requirements that the test elements be of the same material as the structure being tested or that the test elements be cracked, notched, or otherwise structurally weakened to ensure that the test element experienced material failure before the structure being tested. Similarly, U.S. Pat. No. 3,786,679 issued to Crites (1974), U.S. Pat. No. 4,639,997 issued to Brull (1987), or 5,355,734 issued to Kajino (1994) were limited by the requirement(s) that the test elements be of the same material as the structure being tested or that the test elements be "cracked," "notched," or otherwise structurally weakened to ensure that the test element experienced material failure before the structure being tested.

Those which embodied multidirectional monitoring or indicating devices such as the device taught by U.S. Pat. No. 6,443,018 B1 issued to Lee et al.(2002) were limited in that they were designed to only measure or monitor structures with different lengths of artificial cracks or structures with a "weak point" such as a welded joint. Other gauges containing multiple test elements such as that taught by U.S. Pat. No. 4,081,993 issued to Leonhardt et al. (1978) were limited in that they were designed to measure compressive stress only.

Structural and design engineers had concerns in the laboratory as well. The relationship between applied stress and service life of any given structural material or component is typically shown by plotting the applied stress ("S") on a structural material or component against the number of cyclic applications ("N") required to induce failure at that particular stress level. In order to obtain the S-N curve of any new material or composite material for which failure data is not available, test engineers have typically fabricated that material or composite into a test element as suggested by the American Society of Testing Materials ("ASTM") handbook. These test engineers would then subject those specimens to cyclic loads of constant magnitude until the specimen failed. This process would then be repeated upon another specimen which would be subjected to repetitive cyclic loads of induced stress of a different magnitude until failure occurred. Test engineers would repeat these tests until they were able to obtain an acceptable number of data points to determine that material's performance under a number of load conditions. These repetitive tests were costly and time-consuming.

OBJECTS AND ADVANTAGES

The disclosed fatigue measurement device has been designed to solve the foregoing problems found in the prior art. Accordingly, the objects and advantages of the present invention are to provide a fatigue strength and fatigue damage indicator:

(1) that is capable of measuring fatigue strength and fatigue damage in any direction rather than only along the axis of the applied stress.

(2) that will dramatically reduce the number of tests required to graph the S-N curve for any material or composite material being tested.

(3) that may be constructed of the same material or a material other than that of the structure being tested.

(4) that can be used on new structures as well as structures already in service or having some type of prior stress history.

(5) that can measure expended fatigue life of a structure discretely.

(6) that does not require artificial weakening of the test elements.

(7) that does not require any special training to operate.

(8) that reliably predicts a structure's remaining service life.

(9) that will reduce service depot or down-time of the structure or component being measured.

Further objects and advantages of my invention will become apparent from a consideration of the drawings and the ensuing description of the invention.

SUMMARY

This invention provides an apparatus and method for measuring the multidirectional fatigue strength and fatigue damage of structures and then predicting the service life remaining in the structure tested. The apparatus is a specially designed fatigue gauge that contains multiple breakable ligaments of either variable length to measure fatigue strength or fatigue damage of metallic, polymeric and composite materials or the same length but different composition to measure the fatigue strength and fatigue damage of certain composite materials.

DRAWINGS

Drawing Figures

| Reference Numerals in Drawings | |
|---|---|
| 1 | test-coupon |
| 2 | slot $S_2$ |
| 3 | slot $S_3$ |
| 4 | slot $S_4$ |
| 5 | slot $S_5$ |
| 6 | slot $S_6$ |

| -continued | |
|---|---|
| Reference Numerals in Drawings | |
| 7 | ligament $L_7$ |
| 8 | ligament $L_8$ |
| 9 | ligament $L_9$ |
| 10 | ligament $L_{10}$ |
| 11 | slot $S_{11}$ |
| 12 | ligament $L_{12}$ |
| 13 | ligament $L_{13}$ |
| 14 | ligament $L_{14}$ |
| 15 | ligament $L_{15}$ |
| 16 | slot $S_{16}$ |
| 17 | slot $S_{17}$ |
| 18 | slot $S_{18}$ |
| 19 | slot $S_{119}$ |
| 20 | test structure |
| 21 | bond between coupon and structure |
| 22 | polygonal test-coupon |

DETAILED DESCRIPTION

Description

Figure 1:
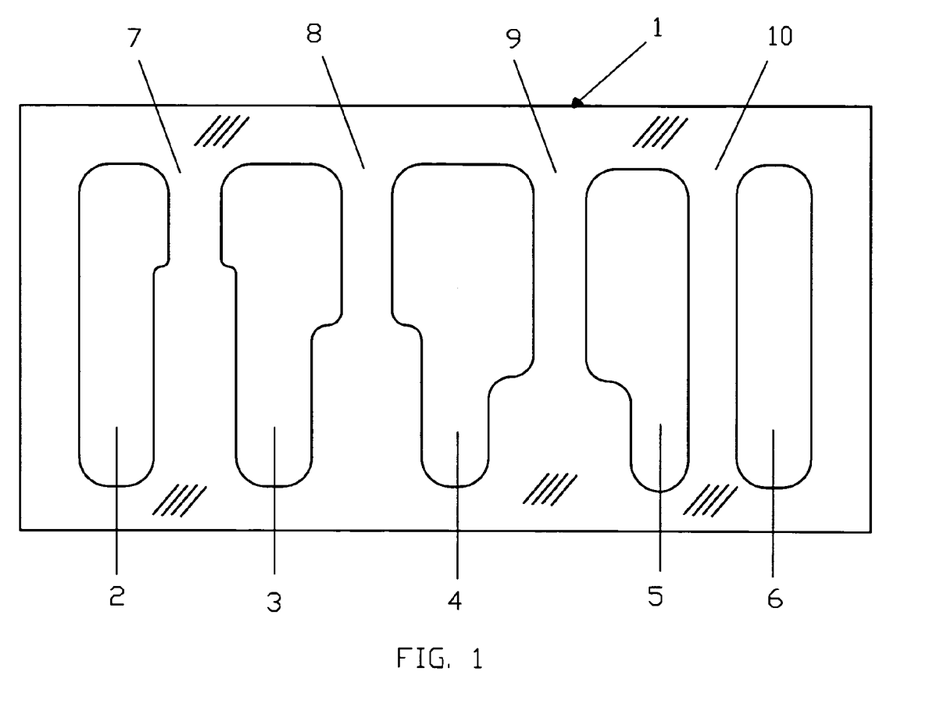
FIG. 1 shows one embodiment of a fatigue-test coupon where the ligaments vary in length and surface area.

FIG. 1 shows an apparatus for measuring fatigue life and fatigue stress on a monitored structure of known composition. The apparatus shown in FIG. 1 is best described as a test-coupon 1 which can be placed upon a test structure 20 selected for stress-fatigue testing and stress-damage testing.

Test-coupon 1 can be fabricated from any suitable material such as aluminum, titanium, stainless steel, copper, etc. which has been rolled into a thin sheet of uniform composition and uniform thickness and then placed under a programmable cutting device. Examples of suitable cutting devices include, without limitation, machine-punches, wire cutting machinery, electro-discharge cutting machinery, laser-cutters, or other such cutting devices which have been configured or programmed to map and cut out slots 2, 3, 4, 5, 6 which define ligaments 7, 8, 9, 10. Typically, computer software associated with any such programmable cutting device will calculate the appropriate dimensions for slots 2, 3, 4, 5, 6 based upon the material from which test-coupon 1 is fabricated.

As mentioned previously, this fatigue measurement device, unlike those taught by the prior art, can be fabricated from any suitable material and, as such, presents a significant advantage over the prior art which typically teaches fatigue measurement devices which must be fabricated from the same material as the structure being tested. The appropriate dimensions for slots 2, 3, 4, 5, 6 will depend upon the material from which test-coupon 1 is fabricated. These dimensions can be calculated by hand and manually entered into a cutting device. These dimensions can also be calculated using computer software associated with and/or part of any such cutting device.

FIG. 1 shows test-coupon 1 with multiple slots 2, 3, 4, 5, 6 defining ligaments 7, 8, 9, 10. The actual number of slots in test-coupon 1 can vary. This gives a test engineer an opportunity to increase testing efficiency by increasing the number of ligaments and thereby reducing the number of cyclic stress tests necessary to obtain sufficient data.

FIG. 1 shows test-coupon 1 having multiple slots 2, 3, 4, 5, 6 with different configurations or shapes. This gives each slot 2, 3, 4, 5, 6 a different surface area ($SSA_2$, $SSA_3$, $SSA_4$, $SSA_5$, $SSA_6$). Accordingly, each ligament 7, 8, 9, 10 on test-coupon 1 shown in FIG. 1 will have a different length ($l_7$, $l_8$, $l_9$, $l_{10}$), a different surface area ($LSA_7$, $LSA_8$, $LSA_9$, $LSA_{10}$), and a different cross-sectional area ($LCSA_7$, $LCSA_8$, $LCSA_9$, $LCSA_{10}$). Because of these variations in dimensions, ligaments 7, 8, 9, 10 will fail due to stress fatigue in sequence from the weakest ligament to the strongest. In this configuration, the dimensions of ligaments 7, 8, 9, 10 are calculated in a manner to ensure that ligaments 7, 8, 9, 10 fail in sequence due to stress fatigue before test structure 20 fails due to stress fatigue when test-coupon 1 and test structure 20 are subjected to substantially the same test history.

As test-coupon 1 is subjected to cyclic stress loads of known or predetermined magnitude, each ligament 7, 8, 9, 10 will experience elongation or contraction equal to that experienced by test structure 20. Because each ligament 7, 8, 9, 10 has a different length, a different surface area, and a different cross-sectional area, each ligament 7, 8, 9, 10 will experience a different amount of induced stress σ and strain ∈ from the same applied load. These different amounts of induced stress σ and strain ∈ vary as functions of the length and cross-sectional area of ligament 7, 8, 9, 10. The weakest ligament experiences the greatest amount of induced stress σ and strain ∈ for a given applied load and will fail before the other ligaments in test-coupon 1. As test-coupon 1 and test structure 20 are subjected to additional cycles of applied loads, the next weakest ligament (which is the next shortest in length) will fail. As additional cycles of applied stress δ are applied, each remaining ligament will fail sequentially from the weakest ligament remaining to the strongest ligament remaining.

Figure 2:
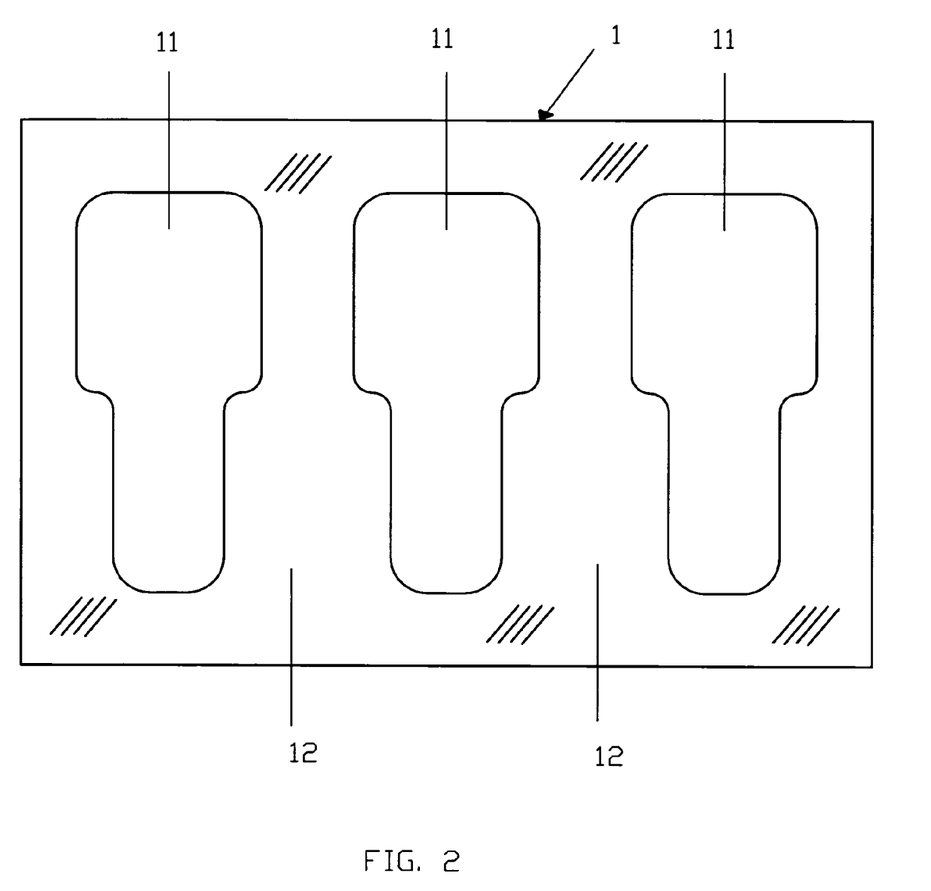
FIG. 2 shows another embodiment of a fatigue-test coupon where the ligaments do not vary in length or surface area.

FIG. 2 shows another embodiment of the fatigue measurement device wherein all slots 11 have the same shape or configuration and, accordingly, the same surface area ($SSA_{11}$). As such, all ligaments 12 will have the same length ($l_{12}$), surface area ($LSA_{12}$), and cross-sectional area ($LCSA_{12}$). In the configuration depicted by FIG. 2, the composition of test-coupon 1 would be varied so that the elastic modulus of each ligament 11 would have a different value. As such, the ligament with the highest elastic modulus would fail under cylic loading before other ligaments having lower elastic moduli because the higher elastic modulus induces a higher stress in that particular ligament. Test-coupon 1 might be used for fatigue strength testing and fatigue damage testing in a scenario where more history is available on a test structure 20. Test-coupon 1 might also be used in this configuration to provide a warning or other indication that test structure 20 has reached a certain milestone in its service life.

The fatigue measuring device depicted by FIG. 2 can also be fabricated from any suitable material and, therefore, also presents a significant advantage over the prior art. The appropriate dimensions for slot 11 and ligament 12 will depend upon the material from which test-coupon 1 is fabricated. These dimensions can be calculated by hand and manually entered into a cutting device. These dimensions can also be calculated using computer software associated with and/or part of any device used for cutting out slot 11.

Figures 3A, 3B:
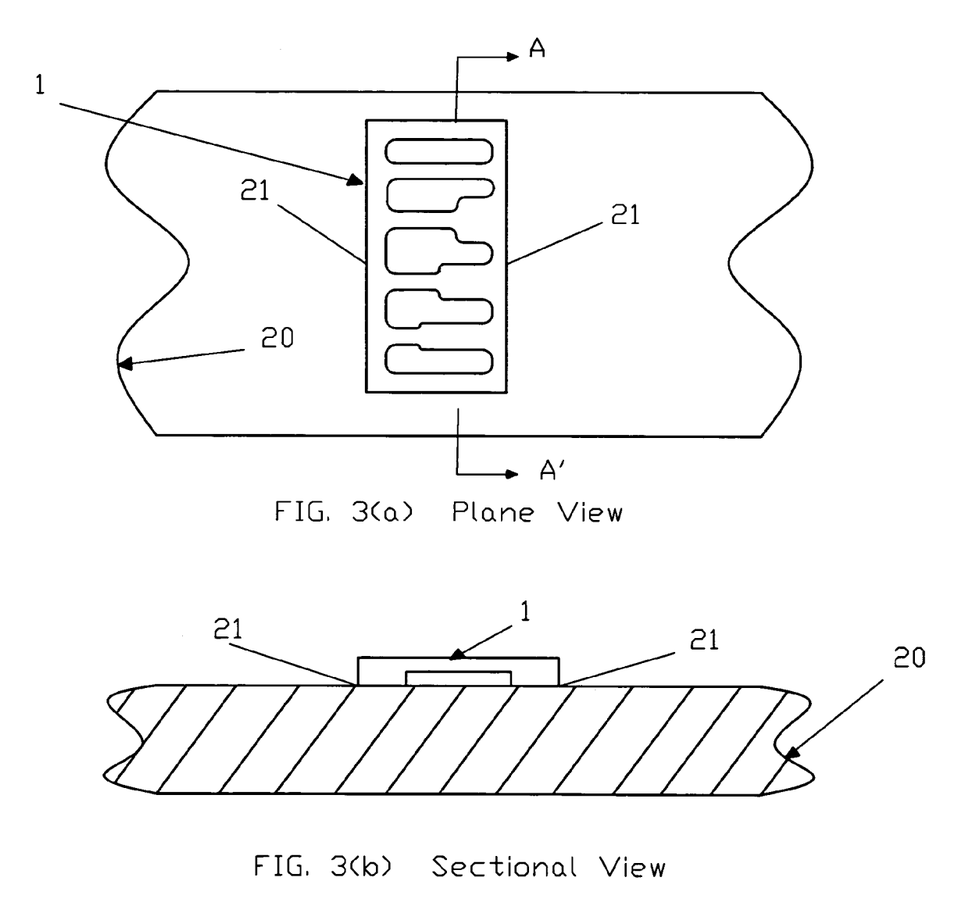
FIGS. 3a and 3b show plan and sectional views of a fatigue-test coupon which has been attached to a structure to measure fatigue damage and fatigue strength along the axis of the applied stress.

FIG. 3*a* shows a plan view of test-coupon 1 attached to test structure 20. FIG. 3*b* shows a cross-section of test-coupon 1 attached to test structure 20. Any type of securing technique that is compatible with test-coupon 1 and test structure 20 may be used to create bond 21. Compatible securing techniques include, without limitation, methods such as welding and the use of adhesive bonding compounds.

Figure 4:
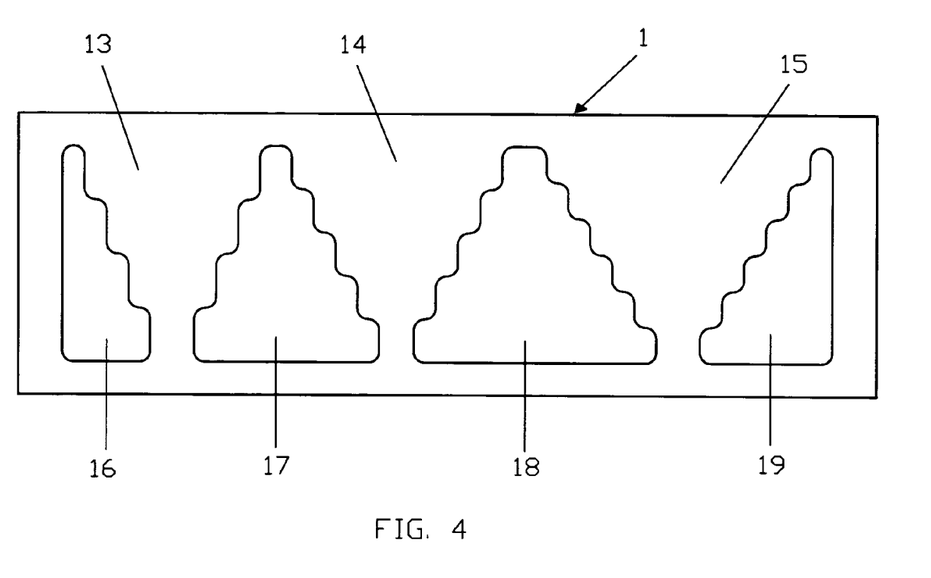
FIG. 4 shows another embodiment of a fatigue-test coupon where the ligaments vary in length and surface area.

FIG. 4 shows an embodiment of test-coupon 1 that is a variation of the embodiment depicted in FIG. 1. FIG. 4 shows test-coupon 1 having multiple slots 16, 17, 18, 19 with different configurations or shapes that have been cut or fabricated using a stepped template. This gives each slot 16, 17, 18, 19 a different surface area ($SSA_{16}$, $SSA_{17}$, $SSA_{18}$, $SSA_{19}$). Accordingly, each ligament 13, 14, 15 on test-coupon 1 shown in FIG. 4 will have a different length ($l_{13}$, $l_{14}$, $l_{15}$) a different surface area ($LSA_{13}$, $LSA_{14}$, $LSA_{15}$), and a different cross-sectional area ($LCSA_{13}$, $LCSA_{14}$, $LCSA_{15}$).

Because of these variations in dimensions, ligaments 13, 14, 15, like those depicted in FIG. 1, will fail due to stress fatigue in sequence from the weakest ligament to the strongest. In this configuration, the dimensions of ligaments 13, 14, 15 are calculated in a manner to ensure that ligaments 13, 14, 15 fail in sequence due to stress fatigue before test structure 20 fails due to stress fatigue when test-coupon 1 and test structure 20 are subjected to substantially the same test history.

The use of a stepped template to cut slots 16, 17, 18, 19 gives the test engineer more control in ordering small-scale variations in the dimensions of slots 16, 17, 18, 19. While the configuration shown in FIG. 1 would typically be used to measure and monitor fatigue stress and fatigue damage over a large range of value, the configuration depicted in FIG. 4 would typically be used to measure and monitor fatigue stress and fatigue damage over a much narrower range of values, thereby giving the test engineer a more accurate picture of a critical range of values.

Figure 5:
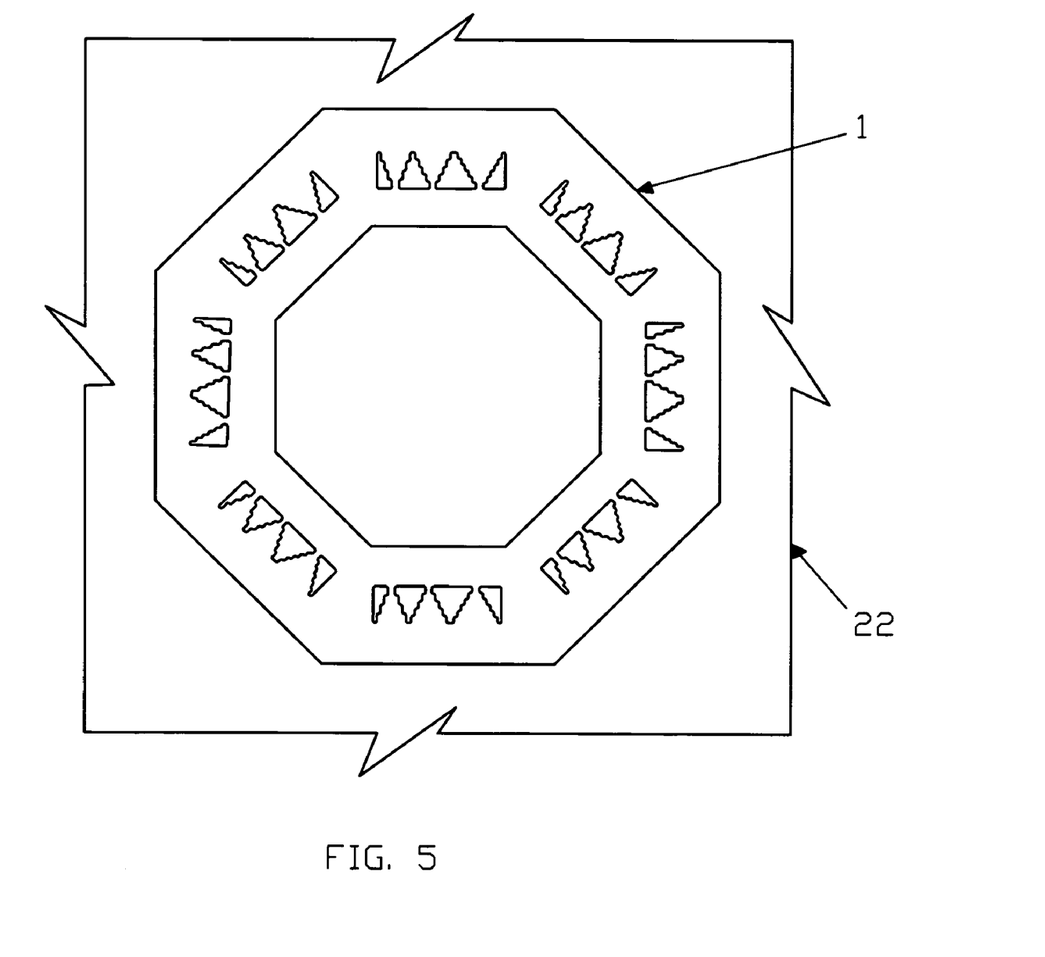
FIG. 5 shows a plan view of another embodiment wherein the fatigue test-coupon has a polygonal configuration and has been attached to a structure to measure multidirectional fatigue damage and fatigue strength.

FIG. 5 shows the preferred embodiment of the invention whereby a differently configured test-coupon 22 is used for measuring stress fatigue and stress damage when the principal loading direction is unknown or when the principal loading direction changes as a function of time. The shape of test-coupon 22 can be a polygon or a circle. By increasing the number of sides on a polygonal test-coupon 22, a test engineer can increase the number of axes or directions along which stress fatigue and stress damage can be measured and thereby increase the accuracy of the measurements.

Figure 6:
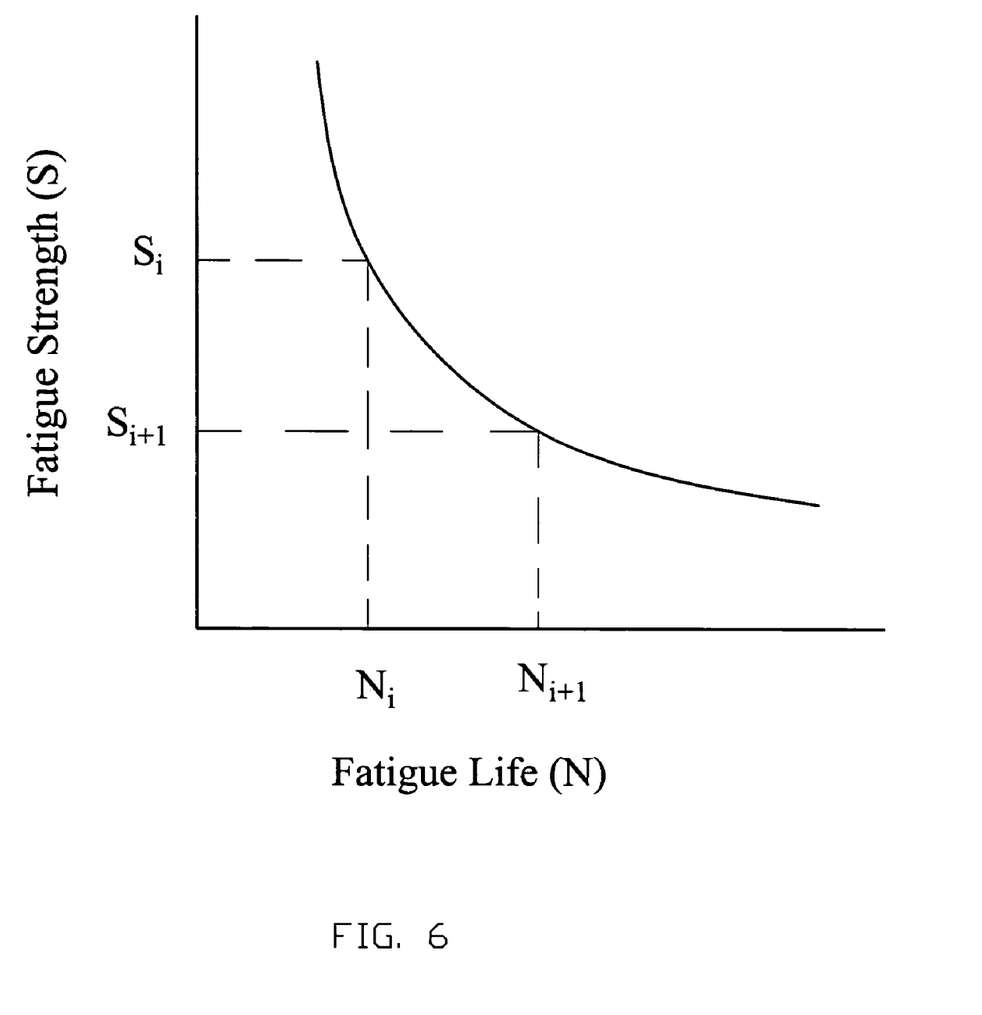
FIG. 6 shows a typical fatigue life curve generally called the S-N curve wherein $S_i$ and $S_{i+1}$ correspond to applied stress levels and $N_i$ and $N_{i+1}$ correspond to the number of applied load cycles.

FIG. 6 shows a typical fatigue life curve generally called the S-N curve wherein $S_i$ and $S_{i+1}$ correspond to applied stress levels and $N_i$ and $N_{i+1}$ correspond to the number of applied load cycles for failure. Any material used to fabricate structural members or the apparatus contemplated by this disclosure will have a unique fatigue life curve which provides an indication of the number of load cycles which will induce fatigue failure as a function of the applied stress. Accordingly, the representative material to which the S-N curve depicted by FIG. 6 applies will experience failure due to stress fatigue if it is subjected to a level $S_i$ for $N_i$ cycles. Similarly, this same material will experience failure due to stress fatigue if it is subjected to a different level of stress, $S_{i+1}$ for a different number, $N_{i+1}$ cycles. The shape of the S-N curve more accurately reflects the fatigue life of the material being tested as the number of different values of induced stress increases because more data points are available to the test engineer.

OPERATION

The fatigue measuring device relies upon the principle that any given material subjected to cyclic stress loads of known magnitude will eventually experience failure due to stress fatigue at a predetermined point; i.e., a known number of repetitive loading cycles. If the magnitude of the cyclic stress load is changed, that given material will experience failure due to stress fatigue after a different number of repetitive loading cycles.

In operation, test-coupon 1 is mounted on test structure 20 and located in such a manner as to experience the same strain history and environment as that experienced by test structure 20. Attachment of test-coupon 1 to test structure 20 can be accomplished by means of pins, adhesive bonds or welding. Unlike most of the test-coupons taught by the prior art, test-coupons 1 does not need to be mounted at any critical location of test structure 20. However, test-coupon 1 should be mounted in such a manner so as to experience the same strain history and environment as test structure 20. Typically, the axis of test-coupon 1 is oriented in the direction of maximum principal tensile strain which is anticipated on test structure 20.

As test-coupon 1 is subjected to cyclic stress loads of known or predetermined magnitude, each one of ligaments 7, 8, 9, 10 will experience the same amount of elongation or contraction as test structure 20. Because each ligament 7, 8, 9, 10 has a different length and cross-sectional area, each ligament 7, 8, 9, 10 will experience a different amount of induced stress $\sigma$ and strain $\in$ from the same applied load. These different amounts of induced stress $\sigma$ and strain $\in$ are vary as functions of the length and cross-sectional area of ligament 7, 8, 9, 10. The weakest ligament experiences the greatest amount of induced stress $\sigma$ and strain $\in$ for a given applied load and will fail before the remaining ligaments. As test coupon 1 and structure being tested 20 are subjected to additional cycles of an applied load, the next weakest ligament will fail. As additional cycles of an applied load are experienced by test coupon 1 and structure being tested 20, each remaining ligament will fail sequentially from the weakest remaining ligament to the next-weakest remaining ligament and so on until all ligaments have failed.

For example, compare ligament 7 to ligament 10 on test-coupon 1 as depicted in FIG. 1. The overall length of ligament 7 ($l_7$) is the sum of the lengths of the upper portion of ligament 7 ($l_{7u}$) and the lower portion of ligament 7 ($l_{7l}$); the length of ligament 10 is ($l_{10}$). Similarly, the cross-sectional area of ligament 7 is broken down into two components: that of the upper portion of ligament 7 ($CSA_{7u}$) and that of the lower portion of ligament 7 ($CSA_{7l}$); the cross-sectional area of ligament 10 is ($CSA_{10}$). When both ligaments 7, 10 have the same displacement $\delta$, the strain or stress ratio for ligaments 7, 10 is:

$$\epsilon_{7u}/\epsilon_{10}=\sigma_{7u}/\sigma_{10}=(CSA_{7l}L_{10})/(CSA_{7u}L_{7l}+CSA_{7l}L_{7u})$$

where $\epsilon_{7u}$ is the strain in the upper portion of ligament 7, $\epsilon_{10}$ is the strain in ligament 10, $\sigma^{7u}$ is the stress in the upper portion of ligament 7 and $\sigma_{10}$ is the stress in ligaments 10. If $L_{7u}=L_{7l}=L_{10}/2$ and $CSA_{7u}=CSA_{7l}/2$, then the strain and the stress in the upper portion of ligament 7 are 1.3 times larger than those found in ligament 10. Accordingly, ligament 7 will fail earlier than ligament 10 because it is under the highest strain and stress. By proper combination of the variable properties of ligaments, 7, 8, 9, 10, the induced stress and strain ratios of all ligaments 7, 8, 9, 10 can be determined for a given displacement. In general, each ligament 7, 8, 9, 10 may have multiple ligament portions or sections of different lengths and cross-sectional areas. Controlling the lengths and cross-sectional areas will permit the test engineer to achieve his desired ratios of induced stress and induced strain for each ligament 7, 8, 9, 10 portion or section.

The induced stress ratio and induced strain ratio will determine when each ligament 7, 8, 9, 10 will fail under fatigue loading. The ligament with the highest stress will fail first, followed by the ligament with the next highest stress, and so on. Careful design of ligaments 7, 8, 9, 10 in test coupon 1 will permit discrete determination of present service life of test structure 20. More ligaments on test-coupon 1 will permit the test engineer to determine service life in smaller (more accurate) intervals.

In laboratory operation, test engineers would typically use the device shown in FIG. 1 to obtain the data points necessary to plot the S-N curve for a new material. Test-coupon 1 is fabricated using the new material and then subjected to cyclic load testing. A given load condition ("S") is plotted on the vertical axis of the S-N curve while the number of cycles ("N") required to cause failure at that given load condition is plotted on the horizontal axis. A second load condition ("S+1") is then plotted on the vertical axis while the number of cycles (N+1) required to cause failure at that different load condition (S+1) is plotted on the horizontal axis. The test engineer will plot enough data points to determine service life under whatever range of loading conditions are mandated by the anticipated use of the material being tested.

The reader should note that using the test-coupon 1 depicted in FIG. 1 will permit test engineers to obtain multiple data points on the S-N curve from a single fatigue cycle loading test. The number of data points on a given S-N curve will correspond to the number of ligaments in a test coupon. Increasing the number of ligaments will increase the number of data points on the S-N curve and thereby, increase its utility over a greater range of values. This aspect of this invention is a significant improvement over the prior art which required multiple fatigue cycle loading tests to obtain sufficient data points on the S-N curve.

Otherwise, test structure 20 is selected or identified for stress-fatigue testing and stress-damage testing. The stress history of test structure 20 is entered on the S-N curve applicable to the material of which test structure 20 is composed. For example, if test structure 20 is composed of aluminum, the number of stress cycles ("N") to which test structure 20 had been subjected as of the test date would be entered on the horizontal axis of the S-N Curve for aluminum. For any given loading condition, the number of cycles remaining ("$N_R$")would be determined by locating the point on the aluminum S-N curve that corresponds to the given or anticipated loading condition ("$S_A$") and reading off the horizontal axis the corresponding number of cycles at which failure would occur ("$N_A$"). The difference between "$N_A-$", and "N" is the remaining service life of test structure 20.

CONCLUSION, RAMIFICATIONS, AND SCOPE

Accordingly, the reader will see that the invention described above provides single-directional and multi-directional fatigue measurement devices which are capable of measuring the actual degree of fatigue damage more accurately and more efficiently than those taught by the prior art. The invention described above provides numerous additional advantages over those taught by the prior art, including, without limitation:

This device is capable of measuring fatigue strength and fatigue damage in any direction as well as along the axis of the applied stress.

This invention will save time and money for test engineers because:
(1) it will dramatically reduce the number of tests required to graph the S-N curve for any material or composite material being tested.
(2) it does not require artificial weakening of the test elements.

(3) it does not require any special training to operate.

(4) it reliably predicts a structure's remaining service life.

Accordingly, this invention will reduce service depot or down-time of the structure or component being measured.

This invention provides the test engineer with greater flexibility because:

(1) the test coupon(s) may be constructed of the same material or a material other than that of the structure being tested.

(2) it can be used on new structures as well as structures already in service or having some type of prior stress history.

(3) it can measure expended fatigue life of a structure discretely.

Although the description above contains many specificities, these should not be interpreted as limiting the scope of the invention but as merely providing illustrations of some of the presently preferred embodiments of this invention. Those skilled in the art will appreciate that various modifications, additions, and substitutions are possible without departing from the scope and spirit of the invention as disclosed in the accompanying claims. Accordingly, the scope of the invention should be determined by the accompanying claims and their legal equivalents, rather than by the examples given.

I claim:

1. An apparatus for measuring the fatigue life of a structural member of known composition, said apparatus comprising:
   a. a flat test-coupon uniformly cast and composed of any material mountable on said structural member,
   b. said test-coupon having at least two cut-out portions of different area which define at least two parallel ligaments of different lengths,
   c. said cut-out portions defining said ligaments having a shape described by at least two centrally aligned adjoining rectangles of different surface area, said centrally aligned adjoining rectangles having rounded corners described by ninety degree arcs joining any two adjacent sides and positioned so that said centrally aligned adjoining rectangles become progressively smaller in surface area, and
   d. said ligaments having a shape so as to effect failure due to fatigue of said ligaments at lower percentages of fatigue life of said structural member and prior to failure of said structural member due to fatigue when said ligament and said structural member are subjected to substantially similar stress conditions and history.

2. The apparatus according to claim 1 wherein said test coupon is composed of a material other than that composing said structural member.

3. A method for determining the remaining useful fatigue life of a structural member of known composition with known fatigue loading history comprising the steps of:
   a. providing a test-coupon uniformly cast and composed of the same material as that comprising said structural member, said test-coupon having at least two cut out portions of different area which define at least two parallel ligaments of different lengths,
   b. subjecting said test-coupon to repetitive stress loading of a constant displacement until all of said ligaments in said test-coupon fail,
   c. monitoring said test-coupon to determine how many loading cycles are necessary to cause failure in each of said ligaments, and
   d. using number of loading cycles necessary to cause failure in each of said ligaments to determine fatigue strength of each of said ligaments and to predict remaining useful service life of said structural member on the basis of an S-N curve depicting stress loading characteristics of material from which said structural member is composed.

4. The method according to claim 3 wherein said cut-out portions are rectangular in shape having rounded corners described by ninety degree arcs joining any two adjacent sides such that said ligaments are all of equal length and width.

5. The method according to claim 3 wherein said cut-out portions defining said ligaments have a shape described by at least two centrally aligned adjoining rectangles of different surface area, said centrally aligned adjoining rectangles having rounded corners described by ninety degree arcs joining any two adjacent sides and positioned so that said centrally aligned adjoining rectangles become progressively smaller in surface area.

6. An apparatus for multidirectional measurement of fatigue life of a structural member of known composition, said apparatus comprising:
   a. a flat test-coupon uniformly cast and composed of any material mountable on said structural member,
   b. said test-coupon having at least two groupings of at least two cut-out portions of different area which define at least two parallel ligaments of different lengths,
   c. said ligaments having a shape so as to effect failure due to fatigue of said ligaments at lower percentages of fatigue life of said structural member and prior to failure of said structural member due to fatigue when said ligament and said structural member are subjected to substantially similar stress conditions and history, and
   d. said groupings arranged such that said parallel ligaments in any said grouping will not be parallel to said parallel ligaments in any other said grouping in said test-coupon.

7. The apparatus according to claim 6 wherein said test coupon is composed of a material other than that composing said structural member.

8. The apparatus according to claim 6 wherein said cut-out portions are rectangular in shape having rounded corners described by ninety degree arcs joining any two adjacent sides such that said ligaments are all of equal length and width.

9. The apparatus according to claim 8 wherein said test coupon is composed of a material other than that composing said structural member.

10. The apparatus according to claim 6 said cut-out portions define said ligaments to have a shape described by at least two adjoining rectangles of different surface area:
    a. positioned so that each successively smaller rectangular portion of said ligament is centered on the next larger adjoining rectangular portion of said ligament, and
    b. having rounded corners described by ninety degree arcs joining any two adjacent sides.

11. The apparatus according to claim 10 wherein said test coupon is composed of a material other than that composing said structural member.

12. The apparatus according to claim 6 wherein said test-coupon has at least two cut out portions of equal cross-sectional area and which define at least two ligaments of the same length and the same shape with different elastic moduli.

13. The apparatus according to claim 12 wherein said test coupon is composed of a material other than that composing said structural member.

* * * * *